(12) United States Patent
Koo et al.

(10) Patent No.: US 6,428,575 B2
(45) Date of Patent: Aug. 6, 2002

(54) PROSTHETIC CAGE FOR SPINE

(75) Inventors: Ja Kyo Koo, 17-611 Sangah Apt., 505 Junggye-Dong, Nowon-Gu, Seoul; Jung Soo Han, 105-301 Olympic Apt, Moonjung-Dong, Songpa-Gu, Seoul; Kyung Tae Kim, Seoul; Jung Sung Kim, Seoul; Ki Sik Min, Bucheon; Byung Soo Kim, Seoul; Chan Soo Shin, Seoul; Jae Yong Ahn, Seoul; Chang Hun Jun, Seoul, all of (KR)

(73) Assignees: Ja Kyo Koo; Jung Soo Han, both of Seoul (KR)

( * ) Notice: Subject to any disclaimer, the term of this patent is extended or adjusted under 35 U.S.C. 154(b) by 0 days.

(21) Appl. No.: 09/755,944

(22) Filed: Jan. 5, 2001

(30) Foreign Application Priority Data

Jan. 6, 2000 (KR) ............................. 2000-261

(51) Int. Cl.$^7$ ................................................. A61F 2/44
(52) U.S. Cl. ................................................... 623/17.11
(58) Field of Search ......................... 623/17.11, 17.16, 623/17.15; 606/73

(56) References Cited

U.S. PATENT DOCUMENTS

| | | | |
|---|---|---|---|
| 5,259,398 A | * 11/1993 | Vrespa | ........................ 128/898 |
| 5,683,391 A | 11/1997 | Boyd | |
| 5,772,661 A | 6/1998 | Michelson | |
| 5,904,719 A | * 5/1999 | Errico et al. | .............. 623/17.11 |
| 6,010,502 A | * 1/2000 | Bagby | ........................... 606/61 |
| 6,030,162 A | * 2/2000 | Huebner | ...................... 411/413 |
| 6,071,310 A | * 6/2000 | Picha et al. | .............. 623/17.11 |
| 6,102,948 A | * 8/2000 | Brosnahan, III | ......... 623/17.11 |
| 6,156,037 A | 12/2000 | LeHuec et al. | |
| 6,206,922 B1 | * 3/2001 | Zdeblick et al. | ......... 623/17.11 |
| 6,210,442 B1 | * 4/2001 | Wing et al. | .............. 623/17.11 |
| 6,241,770 B1 | * 6/2001 | Michelson | ................ 623/17.11 |
| 6,287,343 B1 | * 9/2001 | Kuslich et al. | ........... 623/17.11 |
| 6,306,140 B1 | * 10/2001 | Siddiqui | ...................... 606/73 |

FOREIGN PATENT DOCUMENTS

EP         0 374 088 A1  *  4/1989 ............. A61F/2/00

* cited by examiner

Primary Examiner—David H. Willse
Assistant Examiner—Suzette J. Jackson
(74) Attorney, Agent, or Firm—Merchant & Gould P.C.

(57) ABSTRACT

A prosthetic cage for spine adapted to be implanted in an intervertebral disc space between two vertebral bodies in a spine and to accommodate fusion of the disc space, said cage being a tubular body with an internal aperture, an external surface of which having a plurality of wall apertures each perpendicular to the longitudinal axis thereof and communicating with the internal aperture, and dual convex screw threads extended therefrom, such that the cage of the present invention has an advantage that the stability of fixation between the cage and the vertebral body can be achieved by simple variation of its shape.

4 Claims, 3 Drawing Sheets

PROSTHETIC CAGE FOR SPINE

BACKGROUND OF THE INVENTION

1. Field of the Invention

This invention relates to a prosthetic device implanted in vertebrae for treatment or prevention of back pain in patients with ruptured or degenerated intervetebral discs.

2. Description of the Prior Art

The spine of human is constituted of backbone and fibrocartilaginous disc. FIG. 1 shows a lumbar (200) of human, which consists of vertebral body (220), two pedicles (210) and two intervertebral discs (230). The intervertebral disc (230) is frequently referred to as "disc" and consists of annulus fibrous and nucleus pulpous.

Low back pain is known to be caused by collapse of the disc (230) and adverse effects of bearing the majority of the body weight through a damaged unstable vertebral joint. In the past, clinical attention has been focused on relief of a sciatic pain by removal of pressure from a nerve root. This kind of surgical treatment falls into the following groups.

A 1st method is "Excision of the Ruptured Soft Disc". This procedure removes a portion of the disc compressing the spinal nerve and is generally successful in relieving the sciatic leg pain but in more than half the cases, there is a recurrence of back pain. Over a period of time the disc gradually loses height due to the rupture and said loss of height causes the posterior facet joints of the vertebrae to fit incorrectly, resulting in arthritic change in all elements of the spinal segment.

A 2nd method is "Disc Excision With Posterior Fusion". It prevents motion between adjacent vertebrae but does not alter the fact that approximately 90% of the body weight must be transmitted through degenerated discs, causing pain. Further, posterior fusion tends to bring about bony overgrowth, leading to nerve root compression by spinal stenosis.

A 3rd method is "Disc Excision With Anterior Interbody Fusion". In this method, a soft disc is completely excised and replaced with either a patient's own bone (autologous bone) or with transplant. Banked bones (homologous bone) are generally successful if solid fusion can be obtained between adjacent vertebrae bodies, The success rate has been only about 50%.

A 4th method is "Disc Excision With Posterior Lumbar Intervertebral Fusion (PLIF)". This procedure reconstructs a normal anatomic relationship between the bony and the neural structures and has many advantages. However, this procedure has several serious disadvantages in that it is technically very difficult, and is therefore not as successful or widely used as it might be.

In the art of spinal surgery, various devices and methods for interbody fusion have been developed and are described in U.S. Pat. No. 5,772,661 issued Jun. 30, 1998 to Michelson. U.S. Pat. No. 5,683,391 issued Nov. 4, 1997 to Lawrence M. Boyd describes a system for attachment of cylindrical interbody fusion devices to a spinal rod to which bone screws are also attached and anchored in the vertebral bodies. It is desirable that an interbody fusion construct be as stable as possible. Also, it is desirable to use an endoscopic procedure, if possible. U.S. Pat. No. 6,156,037 issued Dec. 5, 2000 is a system for achieving these benefits.

It discloses an interbody fusion cage having an externally threaded stem (119) projecting from a domed outer end (122). In this invention, a contoured plate is provided with an aperture receivable on the stem. The stem threads receive a nut (121) to fix the plate (111) to a cage (112). A plate (111) has additional apertures receiving bone screws anchoring the plate to vertebral bodies (113,114). The plate (111) has a hemispherical surface surrounding the stem-receiving aperture and bearing on the dome, accommodating universal angulation of the plate relative to the cage.

SUMMARY OF THE INVENTION

However, in such devices with an externally threaded cylindrical body, there was a concern in that the body could slide backward or forward to make a fixed state become unstable, resulting in requirement for complicated fixing device.

Therefore, it is an object of this invention to provide a device for overcoming the above-mentioned problem without recourse to complicated device.

According to one feature of the invention, a prosthetic cage for spine, which is adapted to be implanted in the intervertebral disc space between two vertebral bodies in a spine and to accommodate fusion of the disc space, is a tubular body with an internal aperture, and its external surface has a plurality of wall apertures each perpendicular to the longitudinal axis thereof and communicating with the internal aperture, and dual convex screw threads extended therefrom.

According to another feature of the invention, the prosthetic cage for spine has dual convex screw threads, the inclined planes of which are oppositely directed from each other.

According to still another feature of the invention, the prosthetic cage for spine has dual convex screw threads that are spaced apart from each other and wall apertures are available also between the dual convex screw threads.

According to still another feature of the invention, an introduction end portion of the cage has a sharpened section for stimulating an intervertebral disc space.

DESCRIPTION OF THE PREFERRED EMBODIMENT

Figure 1:
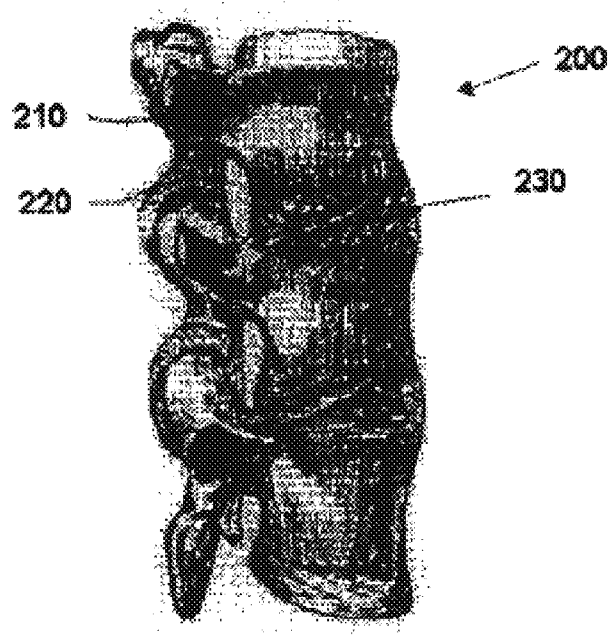
FIG. 1 is a side view of the vertebral column.
Figure 2:
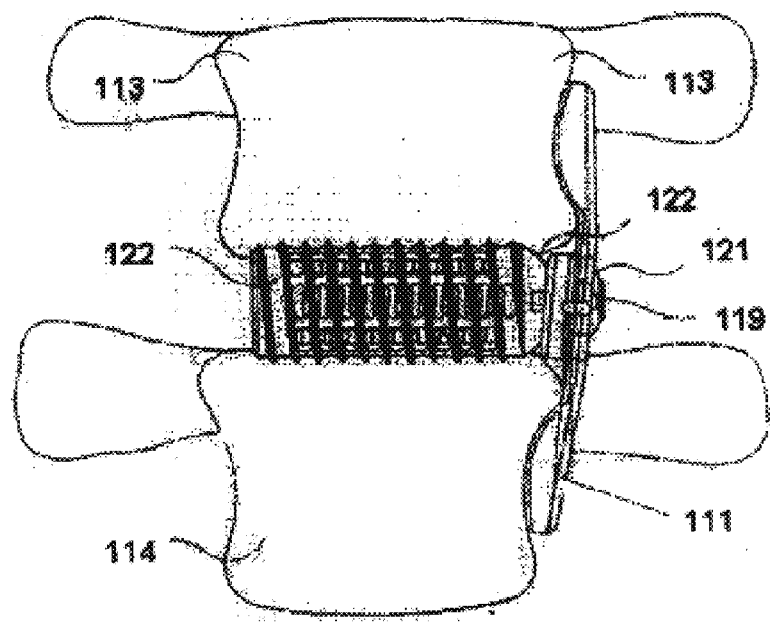
FIG. 2 is a side view of the vertebral column with implants of prior art.

For the purpose of promoting an understanding of the principles of the present invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings wherein like numerals indicate like parts, the cage of this invention is generally indicated by the numeral 1.

Figure 3:
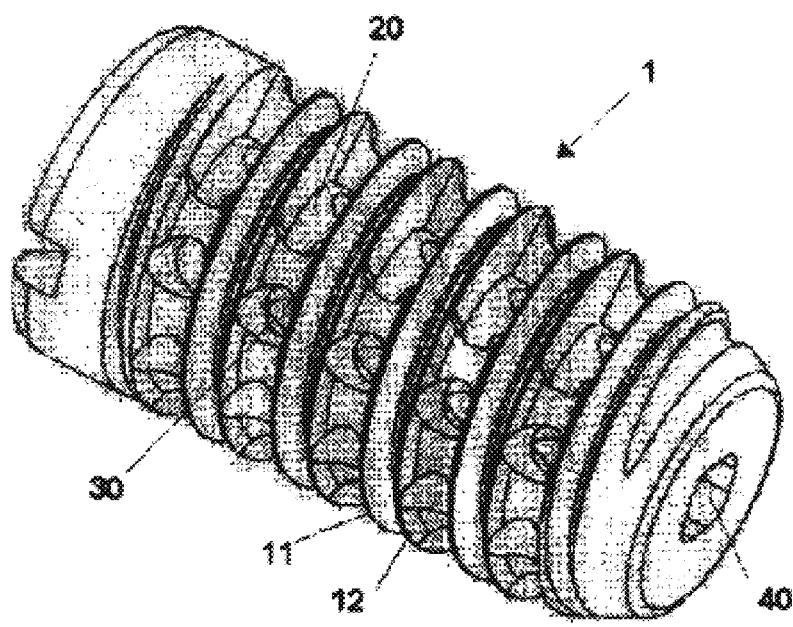
FIG. 3 is a perspective view of one form of prosthetic cage for spine according to the present invention.
Figure 4:
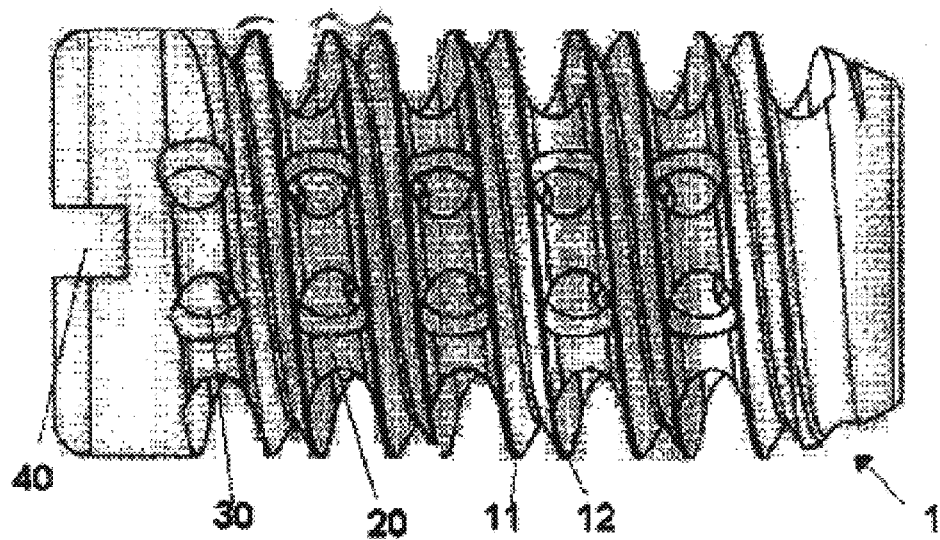
FIG. 4 is a side view of FIG. 3

FIGS. 3 and 4 each show an example of prosthetic cage for spine according to the present invention. The prosthetic cage 1 for spine according to the present invention has a tubular body 20. The tubular body 20 is elongate and has an internal aperture formed in a longitudinal direction of the tubular body 20.

An external surface of the tubular body 20 has convex screw threads 11,12 which are expanded from the external surface of the tubular body 20. The screw threads 11,12 are dual and coupled therebetween. In the example, the two screw threads 11,12 are slightly inclined and the inclined plane of the two screw threads is oppositely directed.

On the other hand, remaining external surface of the tubular body 20 contains a plurality of wall apertures 30. The wall apertures 30 are each perpendicular to the longitudinal axis of the tubular body 20 and communicate with the above internal aperture 40.

In operation, before inserting the cage 1 into the adjacent vertebrae bodies, transverse opposed channel should be cut in the disc space between spaced opposed faces of the adjoining vertebrae bodies with peripheral hard cortex bone surrounding soft cancellous bone.

The above cage 1 is screwed through said open ends of the transverse channels into the disc space 230 of a patient from posterior side of the adjacent vertebrae bodies. For installation in the intervertebral space, the cage 1 is guided and installed in the space in the usual manner, using a general installation tool such as a handle for turning the cage into the space 230.

During the above process, the threads 11,12 scratch the inner wall of the disc space 230 and the fragments of ingrowth materials are cumulated into the internal aperture inside tubular body 20 through the wall apertures 30 which communicate with the internal aperture 40.

In the present invention, the external screw threads 11,12 are dually formed, such that the fixation between the cage 1 and the disc space 230 could be more rigid, compared with the case where the external screw thread of the cage 1 is single.

Further, the coupled screw threads 11,12 may be formed in such a way that their incident planes are opposed each other. In this case, once the cage 1 is located correctly in the channel, the movement of the cage 1 is further prevented to make the setting state of the cage 1 become more stable.

Figure 5:
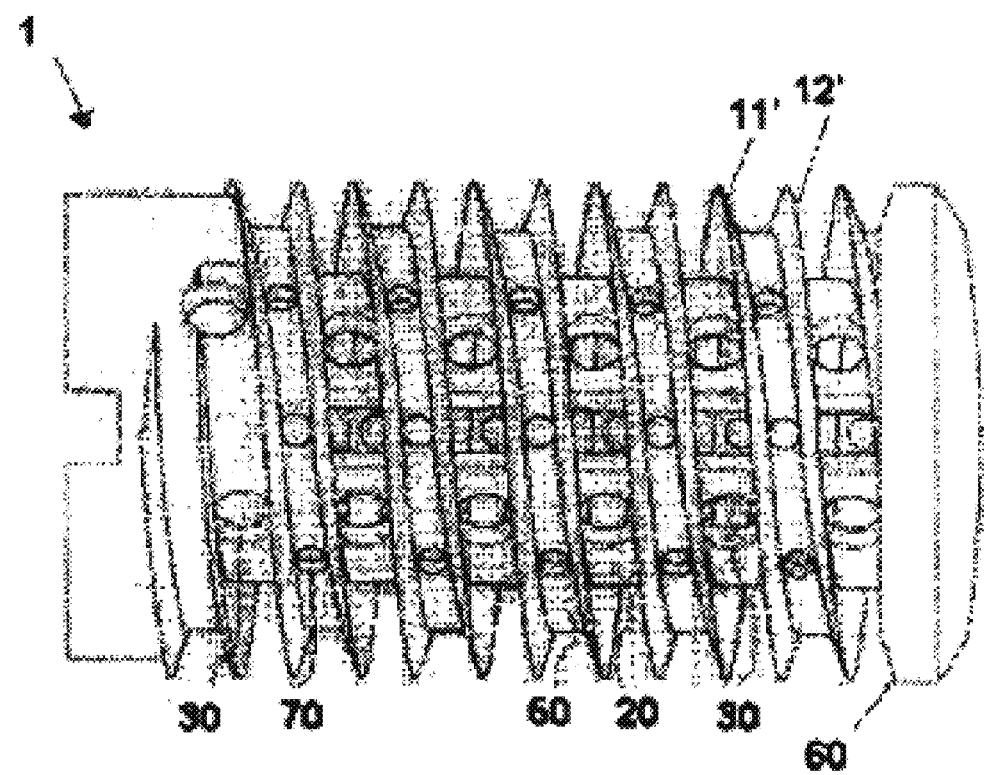
FIG. 5 is a side view of another form of prosthetic cage for spine according to the present invention.

FIG. 5 shows another example of the present invention In this example, the coupled dual screw threads 11', 12' are spaced each other and the spaced surface 50 between the dual screw threads 11', 12'also has wall apertures 70.

On the other hand, in this example, the cage 1 has a sharpened section 60 on a first end of the cage 1 which enters the transverse channel formed in the disc space 230.

The sharpened section 60 is so formed as to stimulate the inner wall of the intervertebral disc space 230 when the cage 1 goes inside the channel of the disc space 230. As the cage 1 is screwed into the channel of the disc space 230, it scratches the inner wall of the channel and facilitate the generation of the debris of the disc space 230, so that the bone ingrowth in the cage 1 from the disc spaces 230 is more promoted.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A prosthetic cage for spine adapted to be implanted in an intervertebral disc space between two vertebral bodies in a spine and to accommodate fusion of the disc space, said cage being a tubular body configured to be implanted in an intervertebral disc space with an internal aperture, an external surface of which being a plurality of wall apertures, each perpendicular to the longitudinal axis thereof and communicating with the internal aperture, and dual convex screw threads extended therefrom.

2. The prosthetic cage for spine of claim 1, wherein each inclined plane of said dual convex screw threads is oppositely directed.

3. The prosthetic cage for spine of claim 2, wherein the dual convex screw threads are spaced apart from each other and the wall apertures are also available between the dual convex screw threads.

4. The prosthetic cage for spine of claim 1, wherein a first end of the cage for introduction has a sharpened section for stimulating an intervertebral disc space.

* * * * *